US00PP19268P2

(12) United States Plant Patent
Pieters

(10) Patent No.: US PP19,268 P2
(45) Date of Patent: Sep. 23, 2008

(54) *CHRYSANTHEMUM* PLANT NAMED 'PPP ALB WH06'

(50) Latin Name: *Chrysanthemum morifolium*
Varietal Denomination: PPP ALB WH06

(75) Inventor: Dirk Pieters, Oostnieuwkerke (BE)

(73) Assignee: Paraty BVBA, Oostnieuwkerke (BE)

( * ) Notice: Subject to any disclaimer, the term of this patent is extended or adjusted under 35 U.S.C. 154(b) by 0 days.

(21) Appl. No.: 11/823,267

(22) Filed: Jun. 27, 2007

(51) Int. Cl.
*A01H 5/00* (2006.01)

(52) U.S. Cl. ..... Plt./288
(58) Field of Classification Search ..... Plt./288
See application file for complete search history.

(56) References Cited

U.S. PATENT DOCUMENTS

PP6,680 P * 3/1989 Jordan et al. ..... Plt./288
PP16,843 P2 * 7/2006 Pieters ..... Plt./288
PP16,875 P2 * 7/2006 Pieters ..... Plt./290

* cited by examiner

*Primary Examiner*—Wendy C. Haas

(57) ABSTRACT

A new and distinct *Chrysanthemum* plant cultivar is disclosed, characterized by large decorative type inflorescences, consistent flowering response to short days, blooming consistently after 49 days of short day length, pure white outer ray florets and creamy yellow inner ray florets, free branching habit, and a consistent natural season flowering habit during the last week of September.

1 Drawing Sheet

Latin name of the genus and species: *Chrysanthemum morifolium.*
Variety denomination: 'PPP ALB WH06'.

BACKGROUND OF THE INVENTION

The new cultivar 'PPP ALB WH06' is a product of a cross between the male present 'Bardi' (not patented in the United States) and the female parent 'GEDI THREE SIE' (U.S. Plant Pat. No. 16,875). The new cultivar was discovered and selected by Dirk Pieters in September of 2002 in Oostnieuwkerke, Belgium.

Asexual reproduction of the new cultivar 'PPP ALB WH06' by terminal cuttings was performed in Oostnieuwkerke, Belgium and Oxnard, Calif., and has shown that the unique features of this new cultivar are stable and reproduced true to type on successive generations.

SUMMARY OF THE INVENTION

The cultivar 'PPP ALB WH06' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'PPP ALB WH06.' These characteristics in combination distinguish 'PPP ALB WH06' as a new and distinct *Chrysanthemum* cultivar:

1. Large, white decorative-type inflorescences with a creamy yellow center;
2. Free branching habit;
3. Consistent natural season flowering habit during the last week of September; and
4. Consistent flowering response to short days, blooming consistently after 49 days of short day length.

Plants of the new cultivar 'PPP ALB WH06' are similar to plants of the male parent variety, 'Bardi' in most horticultural characteristics; however plants of the new cultivar 'PPP ALB WH06' are taller and wider. Also, the new cultivar 'PPP ALB WH06' has more inflorescences per lateral branch. Finally, 'PPP ALB WH06' naturally blooms three weeks earlier.

Plants of the new cultivar 'PPP ALB WH06' are similar to plants of the female parent variety, 'GEDI THREE SIE' in most horticultural characteristics; however plants of the new cultivar 'PPP ALB WH06' are shorter in height. Also, the new cultivar 'PPP ALB WH06' blooms three to four weeks later. Additionally, the female parent 'GEDI THREE SIE' has more inflorescences per lateral branch. Finally, the inflorescences of 'PPP ALB WH06' are white with a creamy yellow center while the inflorescences of the female parent 'GEDI THREE SIE' are orange.

In comparison to the commercially available variety 'GEDI THREE MIL' (U.S. Plant Pat. No. 16,843), 'PPP ALB WH06' has a wider plant spread. Additionally, the new variety 'PPP ALB WH06' has a smaller inflorescence diameter. Further, the new variety 'PPP ALB WH06' does not have as many inflorescences per lateral branch nor as many ray florets per inflorescence as the comparable variety. Finally, the ray florets of 'PPP ALB WH06' are whiter with a more yellow-orange center than the comparable variety.

BRIEF DESCRIPTION OF THE PHOTOGRAPH

The accompanying photograph illustrates in full color a typical plant of 'PPP ALB WH06' grown in a 2 gallon container. One cutting was used in the pot, planted mid May and grown under outdoor field conditions. The color are as nearly true as is reasonably possible in a color representation of this type.

DETAILED BOTANICAL DESCRIPTION

In the following description, color references are made to The Royal Horticultural Society Colour Chart except where general terms of ordinary dictionary significance are used. The following observations and measurements describe 'PPP ALB WH06' plants grown in Oxnard, Ventura County, Calif., during the months of May through October 2006. The growing temperature ranged from 12° C. to 15° C. at night to 12° C. to 20° C. during the day. Measurements and numerical values represent averages of typical flowering types.

Botanical classification: *Chrysanthemum morifolium* cultivar 'PPP ALB WH06'.
Commercial classification: Garden-type *Chrysanthemum.*

PROPAGATION

Time to Rooting: 7 to 14 days at approximately 21° C.
Root Description: Fine, fibrous.

PLANT

Growth habit: Mounding herbaceous perennial.
Height: Approximately 25 cm.
Plant spread: Approximately 39 cm.
Growth rate: Moderate.
Branching characteristics: Free Branching.
Length of lateral Branches: Approximately 18 cm.
Number of leaves per lateral branch: Approximately 22.
Age of plant described: Approximately 154 days.

FOLIAGE

Leaf:
- *Arrangement.*—Alternate single.
- *Average length.*—Approximately 4 cm.
- *Average width.*—Approximately 1.8 cm.
- *Shape of blade.*—Ovate.
- *Apex.*—Acuminate.
- *Base.*—Attenuate.
- *Attachment.*—Stalked.
- *Margin.*—Serrate.
- *Texture of top surface.*—Lightly pubescent.
- *Texture of bottom surface.*—Lightly pubescent.
- *Leaf internode length.*—Approximately 1 cm.
- *Color.*—Young foliage upper side: Near Yellow-Green 147A. Young foliage under side: Near Yellow-Green 147B. Mature foliage upper side: Near Yellow-Green 147A. Mature foliage under side: Near Yellow-Green 147B.
- *Venation.*—Type: Palmately net. Venation color upper side: Near Yellow-Green 147D. Venation color under side: Near Yellow-Green 147D.

Petiole:
- *Average length.*—Approximately 1.1 cm.
- *Color.*—Near Yellow-Green 147D.
- *Diameter.*—Approximately 0.2 cm.

BLOOM

Inflorescence:
- *Flowering habit.*—Induced by darkness period greater than 13.5 hours, approximately 49 days of appropriate day length required to induced and develop blooms.
- *Inflorescence form.*—Decorative.
- *Natural flowering season.*—Approximately the last week in September.
- *Number of inflorescences per lateral branch.*—Approximately 12.
- *Inflorescence diameter.*—Approximately 5.2 cm.
- *Inflorescence depth.*—Approximately 2 cm.
- *Inflorescence longevity on plant.*—Approximately 28 to 34 days.
- *Persistence.*—Persistent.

Ray florets:
- *Appearance.*—Matte.
- *Texture.*—Smooth.
- *Average number of ray florets per inflorescence.*—165.
- *Shape.*—Oblanceolate.
- *Aspect.*—Flat.
- *Margin.*—Entire.
- *Apex.*—Obtuse.
- *Outer ray floret length.*—Approximately 3.5 cm.
- *Outer ray floret width.*—Approximately 0.8 cm.
- *Inner ray floret length.*—Approximately 1.2 cm.
- *Inner ray floret width.*—Approximately 0.2 cm.
- *Color.*—Upper surface of outer ray floret at first opening: Near Yellow 8C. Upper surface of outer ray floret at maturity: Near White 155B. Upper surface of outer ray floret at fading: Near White 155B. Under surface of outer ray floret at first opening: Near Yellow 8C. Under surface of outer ray floret at maturity: Near White 155B. Under surface of outer ray floret at fading: Near White 155B. Center ray florets: Near Yellow 8C throughout maturity and fading.

Disc florets:
- *Appearance.*—Shiny.
- *Texture.*—Smooth.
- *Average number of florets per disc.*—Approximately 110.
- *Shape.*—Cylindric.
- *Apex.*—Obtuse.
- *Average length.*—Approximately 0.4 cm.
- *Average width.*—Approximately 0.1 cm.
- *Color.*—At first opening: Near Yellow-Green 154D. At maturity: Near Yellow-Green 154B. At fading: Near Yellow-Green 154B.

Peduncle:
- *Length.*—At terminal end (shortest): Approximately 3 cm. At lateral end (longest): Approximately 7 cm.
- *Angle to stem.*—Acute.
- *Strength.*—Moderate.
- *Color.*—Near Green 138A.
- *Habit.*—Upright.
- *Diameter.*—Approximately 0.2 cm.
- *Surface texture.*—Lightly pubescent.

Inflorescence Bud:
- *Length.*—Approximately 1 cm.
- *Diameter.*—Approximately 1.4 cm.
- *Form.*—Globular.
- *Color.*—Between Yellow 8C and Yellow 8D.

Involucral bracts (phyllaries):
- *Appearance.*—Matte.
- *Texture.*—Lightly pubescent.
- *Number.*—Approximately 28.
- *Shape.*—Ovate.
- *Margin.*—Entire.
- *Apex.*—Acute.
- *Length.*—Approximately 1 cm.
- *Width.*—Approximately 0.3 cm.
- *Color.*—Upper side: Near Green 137A. Under side: Near Green 137B.

REPRODUCTIVE ORGANS

Ray florets:

*Number of pistils per floret.*—1.
*Stigma shape.*—2 branched.
*Stigma color.*—Near Yellow 9A.
*Style color.*—Near Yellow-Green 154B.
*Style length.*—Approximately 0.3 cm.
*Stamens.*—Absent.

Disc florets:

*Number of pistils per floret.*—1.
*Stigma shape.*—Cylindric.
*Stigma color.*—Near Yellow-Green 154C.
*Style length.*—Approximately 0.1 cm.
*Style color.*—Near Yellow-Green 154D.
*Number of stamens per floret.*—Approximately 5.
*Anther shape.*—Tubular.
*Anther color.*—Near Yellow-Green 154C.
*Pollen color.*—No pollen detected.

OTHER CHARACTERISTICS

Disease resistance: Neither resistance nor susceptiblity to diseases or pests has been observed in this variety.

Drought tolerance/cold tolerance: Flowering plants are hardy to low temperatures about −2° C. Non-flowering plants are hardy in the approximate range of 3° C. to −6° C. depending upon duration of cold and amount of moisture in the soil. With adequate water plants are hardy to a high temperature of 45° C.

Fruit/seed production: Commercially, this plant is not used or observed in a stage where seeds would be produced. Therefore, seed production has not been observed.

What is claimed is:

1. A new and distinct cultivar of *Chrysanthemum* plant named 'PPP ALB WH06' as herein illustrated and described.

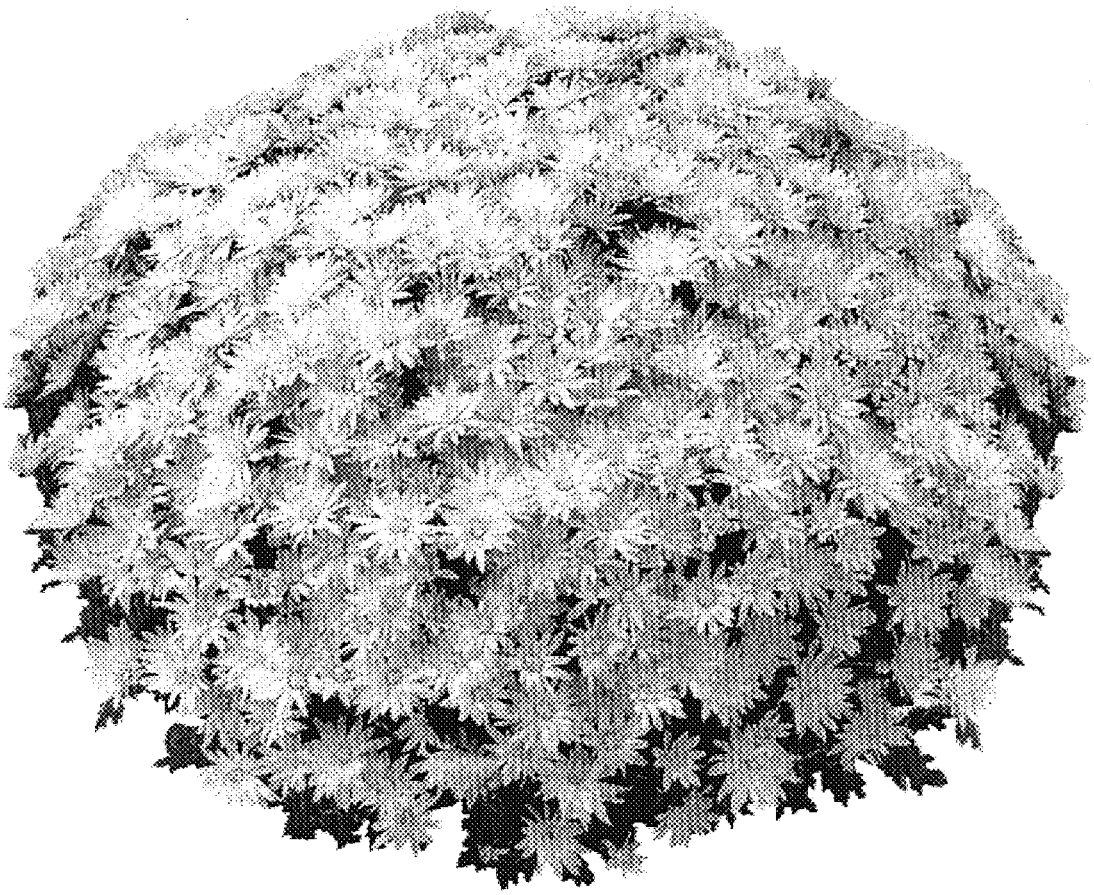

* * * * *